US008993790B2

(12) United States Patent
Son et al.

(10) Patent No.: US 8,993,790 B2
(45) Date of Patent: Mar. 31, 2015

(54) OXETANE-RING-CONTAINING (METH)ACRYLIC ACID ESTER COMPOUND

(75) Inventors: Tamaki Son, Himeji (JP); Kiyoshi Ikura, Himeji (JP)

(73) Assignee: Daicel Corporation, Osaka-Shi (JP)

( * ) Notice: Subject to any disclaimer, the term of this patent is extended or adjusted under 35 U.S.C. 154(b) by 100 days.

(21) Appl. No.: 13/510,144

(22) PCT Filed: Nov. 5, 2010

(86) PCT No.: PCT/JP2010/069689
§ 371 (c)(1),
(2), (4) Date: May 16, 2012

(87) PCT Pub. No.: WO2011/062070
PCT Pub. Date: May 26, 2011

(65) Prior Publication Data
US 2012/0232295 A1 Sep. 13, 2012

(30) Foreign Application Priority Data

Nov. 17, 2009 (JP) .................................. 2009-261507
Nov. 17, 2009 (JP) .................................. 2009-261509

(51) Int. Cl.
| | | |
|---|---|---|
| C07D 493/00 | (2006.01) | |
| C07D 305/06 | (2006.01) | |
| C08G 65/14 | (2006.01) | |
| C08G 65/18 | (2006.01) | |
| C08G 65/26 | (2006.01) | |
| C08F 120/32 | (2006.01) | |
| C09D 133/06 | (2006.01) | |

(52) U.S. Cl.
CPC .............. *C07D 305/06* (2013.01); *C08G 65/14* (2013.01); *C08G 65/18* (2013.01); *C08G 65/2606* (2013.01); *C08F 120/32* (2013.01); *C09D 133/068* (2013.01)
USPC ........................................................ 549/510

(58) Field of Classification Search
CPC .................................................. C07D 305/06
USPC ........................................................ 549/510
See application file for complete search history.

(56) References Cited

U.S. PATENT DOCUMENTS

| | | | | |
|---|---|---|---|---|
| 8,293,448 B2 * | 10/2012 | Ito et al. | .......................... | 430/269 |
| 8,367,702 B2 * | 2/2013 | Onda et al. | ..................... | 514/312 |
| 2005/0181301 A1 | 8/2005 | Matsumura | | |
| 2009/0209674 A1 | 8/2009 | Ito et al. | | |

FOREIGN PATENT DOCUMENTS

| | | |
|---|---|---|
| JP | 2003-137877 A | 5/2003 |
| JP | 2008-224970 A | 9/2008 |
| JP | 2009-256553 A | 11/2009 |
| JP | 2010-217355 A | 9/2010 |
| WO | WO 2007/145309 A1 | 12/2007 |

OTHER PUBLICATIONS

DN 151:200432 (equiv. of KR 2009071812) (2009).*
Extended European Search Report issued Mar. 15, 2013, in European Patent Application No. 10831465.9.
El-Ghayoury et al., "Ultraviolet-Ultraviolet Dual-Cure Process Based on Acrylate Oxetane Monomers"—Journal of Polymer Science A: Polymer Chemistry, (2003), 41(4), 469-475.
International Search Report for PCT/JP2010/069689 dated Feb. 15, 2011.

(Continued)

*Primary Examiner* — Noble Jarrell
*Assistant Examiner* — Raymond Covington
(74) *Attorney, Agent, or Firm* — Birch, Stewart, Kolasch & Birch, LLP

(57) ABSTRACT

Provide is an oxetane-ring containing (meth) acrylic ester compound which can give, through polymerization, a cured article being highly flexible or thermally stable. The oxetane-ring-containing (meth) acrylic ester compound is represented by formula (1) below, in which $R^1$ represents a hydrogen atom or an alkyl group; $R^2$ represent a hydrogen atom or a methyl group; and "A" represent either a linear alkylene group represented by following formula (a1) or a branched-chain alkylene group represented by following formula (a2).

4 Claims, 1 Drawing Sheet

(56) References Cited

OTHER PUBLICATIONS

Motoi et al., "Oxetane Derivatives and Their Polymers for Designing Functional Polymers Containing a Soft, Somewhat Polar Polyether Network as a Polymer Support",—Bulletin of Chemical Society of Japan, vol. 62, No. 5, pp. 1572-1581, 1989.

Motoi M. et al., "Soft Moderately Polar Polyether Networks as a Polymeric Support for Designing Functional Polymers"—Japanese Journal of Polymer Science and Technology, 1989, vol. 46, No. 1, pp. 59-62, Summary Compound 9.

* cited by examiner

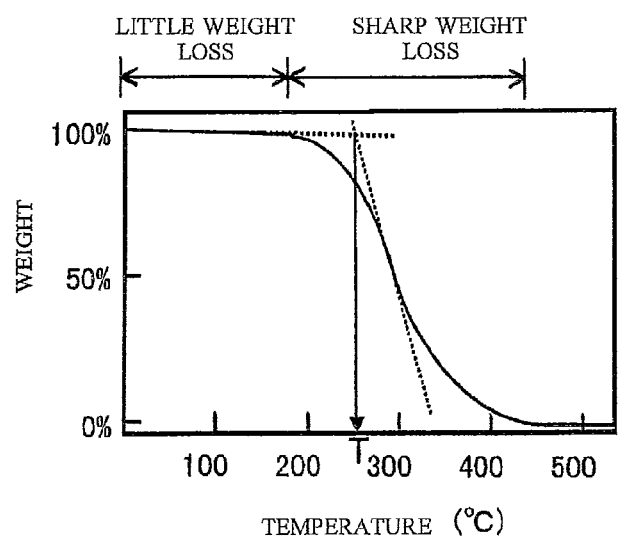

OXETANE-RING-CONTAINING (METH)ACRYLIC ACID ESTER COMPOUND

TECHNICAL FIELD

The present invention relates to oxetane-ring-containing (meth)acrylic ester compounds which have an oxetane ring serving as a cationically polymerizable moiety and a (meth)acryloyl group serving as a radically polymerizable moiety and can give, through polymerization, cured articles excellent in flexibility or thermal stability.

BACKGROUND ART

Examples of known oxetane-ring-containing (meth)acrylic ester compounds include 3-methyl-3-(2-methacryloyloxyethyloxymethyl)oxetane and 3-ethyl-3-(2-acryloyloxyethyloxymethyl)oxetane (see, for example, Patent Literature (PTL) 1 and Non Patent Literature (NPL) 1).

An oxetane-ring-containing (meth)acrylic ester compound may be synthetically prepared by synthesizing a corresponding oxetane-ring-containing alcohol as a precursor, and allowing the prepared oxetane-ring-containing alcohol to react with (meth)acrylic acid. As a process for synthetically preparing such a precursor oxetane-ring-containing alcohol, there is known a process for preparing an oxetane-ring-containing alcohol by allowing 3-ethyl-3-hydroxymethyloxetane to react with a haloalcohol whose hydroxyl group being protected by a protecting group; and subsequently performing deprotection (NPL 1). This process, however, suffers from problems such that the process requires the step of protecting a reactive group and the step of deprotecting the protected reactive group, thereby includes complicated multiple reaction steps, and suffers from a low yield. As a process including not-so-complicated reaction step(s), there is known a process for preparing an oxetane-ring-containing alcohol by allowing 3-ethyl-3-methanesulfonyloxymethyloxetane and a diol to react with each other in the presence of a phase transfer catalyst in a liquid-liquid biphasic system (PTL 2). This process, however, suffers from problems such that a target product is obtained in a low yield because of low reaction selectivity.

Under present circumstances, only few types of oxetane-ring-containing (meth)acrylic ester compounds are known, because it is difficult to efficiently synthetically prepare precursor corresponding oxetane-ring-containing alcohols, as is described above.

CITATION LIST

Patent Literature

PTL 1: Japanese Unexamined Patent Application Publication (JP-A) No. 2008-224970
PTL 2: PCT International Publication Number WO2007/145309

Non Patent Literature

NPL 1: Journal of Polymer Science, Part A: Polymer Chemistry (2003), 41(4), 469-475

SUMMARY OF INVENTION

Technical Problem

Accordingly, an object of the present invention is to provide a novel oxetane-ring-containing (meth)acrylic ester compound which has an oxetane ring serving as a cationically polymerizable moiety and a (meth)acryloyl group serving as a radically polymerizable moiety and can form, through polymerization, a cured article excellent in flexibility or thermal stability.

Another object of the present invention is to provide a process for easily and efficiently producing the novel oxetane-ring-containing (meth)acrylic ester compound.

Solution to Problem

After intensive investigations to achieve the objects, the present inventors found a novel oxetane-ring-containing (meth)acrylic ester compound structurally including an oxetane ring serving as a cationically polymerizable moiety and a (meth)acryloyl group serving as a radically polymerizable moiety bonded to each other through the medium of a linear alkylene group having three or more carbon atoms; and found that this oxetane-ring-containing (meth)acrylic ester compound can form, through polymerization, a cured article excellent in flexibility. They also found another novel oxetane-ring-containing (meth)acrylic ester compound having a tetrasubstituted carbon at the 6-position from the carbon of (meth)acrylic terminus; and found that this oxetane-ring-containing (meth)acrylic ester compound can form, through polymerization, a cured article which has more satisfactory thermal stability than that of a cured article obtained through polymerization of an oxetane-ring-containing (meth)acrylic ester compound including a disubstituted carbon at the 6-position. In addition, they found that oxetane-ring-containing alcohols serving as precursors for the oxetane-ring-containing (meth)acrylic ester compounds can be simply and efficiently synthesized with satisfactory selectivity each by allowing an oxetane compound and a diol to react with each other under specific conditions. The present invention has been made based on these findings.

Specifically, the present invention provides, in an aspect, an oxetane-ring-containing (meth)acrylic ester compound represented by following Formula (1):

[Chem. 1]

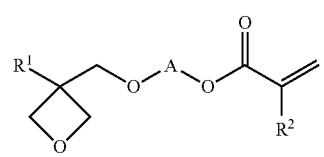

(1)

wherein $R^1$ represents a hydrogen atom or an alkyl group; $R^2$ represents a hydrogen atom or a methyl group; "A" represents either a linear alkylene group represented by following Formula (a1) or a branched-chain alkylene group represented by following Formula (a2):

[Chem. 2]

(a1)

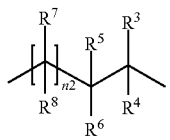

(a2)

wherein, in Formula (a1), n1 denotes an integer of 3 or more, and in Formula (a2), $R^3$, $R^4$, $R^7$, and $R^8$ are the same as or different from one another and each represent a hydrogen atom or an alkyl group; $R^5$ and $R^6$ are the same as or different from each other and each represent an alkyl group; and n2 denotes an integer of 0 or more, wherein, when n2 is an integer of 2 or more, two or more $R^7$s may be the same as or different from one another, and two or more $R^8$s may be the same as or different from one another, and wherein the rightmost end of Formula (a2) is bonded to oxygen atom constituting ester bond.

The present invention provides, in another aspect, a process for producing an oxetane-ring-containing (meth)acrylic ester compound, the process comprising the steps of: allowing two compounds to react with each other in the presence of a basic substance in a single-liquid phase system to give a reaction product; and (meth)acrylating the reaction product to synthetically prepare the oxetane-ring-containing (meth)acrylic ester compound, one of the two compounds being represented by following Formula (2):

[Chem. 3]

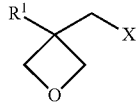

(2)

wherein $R^1$ represents a hydrogen atom or an alkyl group; and X represents a leaving group,
the other compound being represented by following Formula (3):
[Chem. 4]

<p style="text-align:center">HO-A-OH   (3)</p> wherein "A" represents either a linear alkylene group represented by following Formula (a1) or a branched-chain alkylene group represented by following Formula (a2):

[Chem. 5]

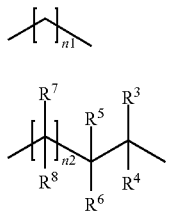

(a1)

(a2)

wherein, in Formula (a1), n1 denotes an integer of 3 or more, and in Formula (a2), $R^3$, $R^4$, $R^7$, and $R^8$ are the same as or different from one another and each represent a hydrogen atom or an alkyl group; $R^5$ and $R^6$ are the same as or different from each other and each represent an alkyl group; and n2 denotes an integer of 0 or more, wherein, when n2 is an integer of 2 or more, two or more $R^7$s may be the same as or different from one another, and two or more $R^8$s may be the same as or different from one another, and the oxetane-ring-containing (meth)acrylic ester compound being represented by following Formula (1):

[Chem. 6]

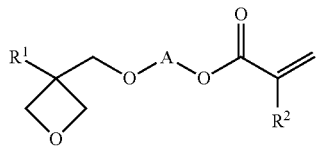

(1)

wherein $R^2$ represents a hydrogen atom or a methyl group; and
$R^1$ and A are as defined above.

Advantageous Effects of Invention

Of the oxetane-ring-containing (meth)acrylic ester compounds represented by Formula (1) according to the present invention, compounds in which "A" is a linear alkylene group represented by Formula (a1) each include an oxetane ring serving as a cationically polymerizable moiety and a (meth)acryloyl group serving as a radically polymerizable moiety bonded to each other through the medium of a linear alkylene group having three or more carbon atoms. These compounds therefore give, through polymerization, cured articles which have a ladder structure of the alkylene group having three or more carbon atoms and can thereby exhibit satisfactory flexibility.

For these reasons, the compounds are advantageously usable typically in the fields of waveguides, optical fibers, base films and protective films for solar cells, base films and protective films for flexible displays, base films and protective films for organic electroluminescent devices, transparent sealants, adhesives, ink-jet inks, color filters, nanoimprinting (materials), and flexible wiring boards.

Of the oxetane-ring-containing (meth)acrylic ester compounds represented by Formula (1) according to the present invention, compounds in which "A" is a branched-chain alkylene group represented by Formula (a2) each include an oxetane ring serving as a cationically polymerizable moiety and a (meth)acryloyl group serving as a radically polymerizable moiety bonded to each other through the medium of a bulky chain structure having a tetrasubstituted carbon at the 6-position from the carbon of acrylic terminus. These compounds can therefore give, through polymerization, cured articles which exhibit more satisfactory thermal stability than that of cured articles obtained from oxetane-ring-containing (meth)acrylic ester compounds having a disubstituted carbon at the 6-position from the carbon of acrylic terminus.

For these reasons, the compounds are advantageously usable typically in the fields of waveguides, optical fibers, base films and protective films for solar cells, base films and protective films for flexible displays, base films and protective films for organic electroluminescent devices, transparent sealants, adhesives, ink-jet inks, color filters, nanoimprinting (materials), and flexible wiring boards. In particular, they are advantageously usable in applications exposed to high-temperature surroundings and guarantee long-term reliability.

The process for producing an oxetane-ring-containing (meth)acrylic ester compound according to the present invention enables efficient production of the novel oxetane-ring-containing (meth)acrylic ester compounds with high selectivity, thereby excels in productivity, and is suitable for industrialization.

BRIEF DESCRIPTION OF DRAWINGS

FIG. 1 is an explanatory drawing (schematic view indicating data of thermogravimetry) illustrating how to evaluate the thermal stability of a cured article.

DESCRIPTION OF EMBODIMENTS

[Oxetane-Ring-Containing (Meth)Acrylic Ester Compounds]

Oxetane-ring-containing (meth)acrylic ester compounds according to embodiments of the present invention are represented by Formula (1). In Formula (1), $R^1$ represents a hydrogen atom or an alkyl group; $R^2$ represents a hydrogen atom or a methyl group; and "A" represents either a linear alkylene group represented by Formula (a1) or a branched-chain alkylene group represented by Formula (a2). In Formula (a1), n1 denotes an integer of 3 or more. In Formula (a2), $R^3$, $R^4$, $R^7$, and $R^8$ are the same as or different from one another and each represent a hydrogen atom or an alkyl group; $R^5$ and $R^6$ are the same as or different from each other and each represent an alkyl group; and n2 denotes an integer of 0 or more. When n2 is an integer of 2 or more, two or more $R^7$s may be the same as or different from one another, and two or more $R^8$s may be the same as or different from one another. The rightmost end of Formula (a2) is bonded to oxygen atom constituting ester bond.

In Formula (1), $R^1$ represents a hydrogen atom or an alkyl group. The alkyl group is preferably any of alkyl groups having 1 to 4 carbon atoms, which are typified by linear alkyl groups having 1 to 4 carbon atoms, such as methyl, ethyl, propyl, and butyl groups, of which those having 1 to 3 carbon atoms are more preferred; and branched-chain alkyl groups having 1 to 4 carbon atoms, such as isopropyl, isobutyl, s-butyl, and t-butyl groups, of which those having 1 to 3 carbon atoms are more preferred. Among them, $R^1$ is particularly preferably methyl group or ethyl group.

"A" represents either a linear alkylene group represented by Formula (a1) or a branched-chain alkylene group represented by Formula (a2). In Formula (a1), n1 denotes an integer of 3 or more. In Formula (a2), $R^3$, $R^4$, $R^7$, and $R^8$ are the same as or different from one another and each represent a hydrogen atom or an alkyl group; $R^5$ and $R^6$ are the same as or different from each other and each represent an alkyl group; and n2 denotes an integer of 0 or more. When n2 is an integer of 2 or more, two or more $R^7$s may be the same as or different from one another, and two or more $R^8$s may be the same as or different from one another. The rightmost end of Formula (a2) is bonded to the oxygen atom constituting the ester bond.

In Formula (a1), n1 denotes an integer of 3 or more and is preferably an integer of from 3 to 20, and particularly preferably an integer of from 3 to 10. A compound in which n1 is less than 3 may give, through polymerization, a cured article which tends to have insufficient flexibility. In contrast, a compound in which n1 is more than 20 may give a cured article which tends to have excessively high flexibility and to have inferior dimensional stability under high-temperature conditions.

In Formula (a2), the alkyl groups as $R^3$, $R^4$, $R^7$, and $R^8$ are preferably alkyl groups having 1 to 4 carbon atoms, which are typified by linear alkyl groups having 1 to 4 carbon atoms, such as methyl, ethyl, propyl, and butyl groups, of which those having 1 to 3 carbon atoms are more preferred; and branched-chain alkyl groups having 1 to 4 carbon atoms, such as isopropyl, isobutyl, s-butyl, and t-butyl groups, of which those having 1 to 3 carbon atoms are more preferred. The groups $R^3$ and $R^4$ herein are preferably hydrogen atoms.

In Formula (a2), $R^5$ and $R^6$ are the same as or different from each other and each represent an alkyl group. Examples of the alkyl group are as in the alkyl groups as $R^3$, $R^4$, $R^7$, and $R^8$. The groups $R^5$ and $R^6$ are each preferably methyl group or ethyl group.

In Formula (a2), n2 denotes an integer of 0 or more and is preferably an integer of from 1 to 20, and particularly preferably an integer of from 1 to 10. A compound in which n2 is more than 20 may give a cured article which tends to have excessively high flexibility and to have insufficient dimensional stability under high-temperature conditions.

Typical examples of oxetane-ring-containing (meth)acrylic ester compounds represented by Formula (1) in which "A" is a linear alkylene group represented by Formula (a1) include the following compounds:

[Chem. 7]

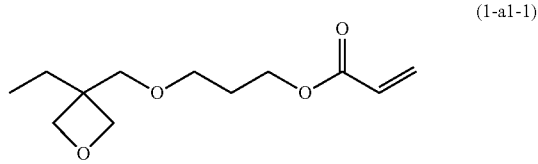

(1-a1-1)

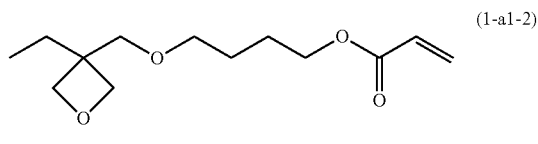

(1-a1-2)

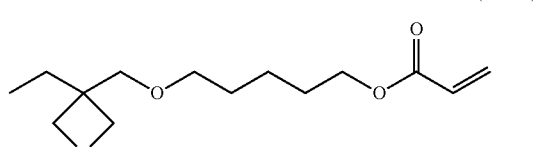

(1-a1-3)

Typical examples of oxetane-ring-containing (meth)acrylic ester compounds represented by Formula (1) in which "A" is a branched-chain alkylene group represented by Formula (a2) include the following compounds:

[Chem. 8]

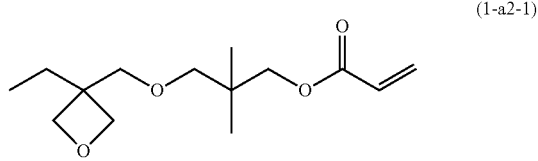 [SMILES: C=CC(=O)OCC(C)(C)COCC1(CC)COC1]

(1-a2-1)

(1-a2-2)

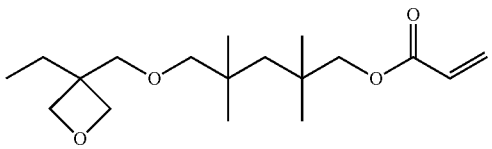

Oxetane-ring-containing (meth)acrylic ester compounds represented by Formula (1) according to the present invention each have an oxetane ring serving as a cationically polymerizable moiety and a (meth)acryloyl group serving as a radically polymerizable moiety and thereby give cured articles through radical polymerization and/or cationic polymerization.

Oxetane-ring-containing (meth)acrylic ester compounds according to the present invention represented by Formula (1) in which "A" is a linear alkylene group represented by Formula (a1) give, through polymerization, cured articles which excel in flexibility, because of having a ladder structure derived from the linear alkylene group having three or more carbon atoms. They are therefore very useful typically in the fields of waveguides (e.g., optical waveguides and photoelectric hybrid wiring boards), optical fibers, base films and protective films for solar cells, base films and protective films for flexible displays, base films and protective films for organic electroluminescent devices, transparent sealants, adhesives, ink-jet inks, color filters, nanoimprinting (materials), and flexible boards; and they are very useful particularly in the fields of flexible optical waveguides, optical fibers, transparent sealants, and nanoimprinting (materials).

Oxetane-ring-containing (meth)acrylic ester compounds according to the present invention represented by Formula (1) in which "A" is a branched-chain alkylene group represented by Formula (a2) each include an oxetane ring serving as a cationically polymerizable moiety and a (meth)acryloyl group serving as a radically polymerizable moiety bonded to each other through the medium of a bulky chain structure. When polymerized, the compounds can therefore form three-dimensionally crosslinked structures to give cured articles which exhibit satisfactory thermal stability. They are therefore very useful in such fields that the cured articles are exposed to heat, and are advantageously used typically in or as waveguides (e.g., optical waveguides and photoelectric hybrid wiring boards), optical fibers, base films and protective films for solar cells, base films and protective films for flexible displays, base films and protective films for organic electroluminescent devices, transparent sealants, adhesives, ink-jet inks, color filters, nanoimprinting (materials), and flexible boards. They are particularly advantageously used typically in or as flexible optical waveguides, optical fibers, transparent sealants, and nanoimprinting (materials).

[Process for Producing Oxetane-Ring-Containing (Meth) Acrylic Ester Compounds]

Each of the oxetane-ring-containing (meth)acrylic ester compounds represented by Formula (1) according to the present invention may be synthetically prepared by allowing a compound represented by Formula (2) and a compound represented by Formula (3) to react with each other in the presence of a basic substance in a single-liquid phase system to give a reaction product, and (meth)acrylating the reaction product.

In Formula (2), $R^1$ corresponds to $R^1$ in Formula (1), may be the same as or different from each other, and represents a hydrogen atom or an alkyl group. Examples as $R^1$ are the same as with $R^1$ in Formula (1). Among them, $R^1$ herein is preferably methyl group or ethyl group.

X represents a leaving group, which is typified by groups having high leaving ability, including halogen atoms such as chlorine, bromine, and iodine; sulfonyloxy groups such as p-toluenesulfonyloxy group, methanesulfonyloxy group, and trifluoromethanesulfonyloxy group; and carbonyloxy groups such as acetyl group. The group X herein is preferably a sulfonyloxy group and particularly preferably methanesulfonyloxy group, for satisfactory reactivity with the compound represented by Formula (3) and for excellent leaving ability.

The compound represented by Formula (2) may be synthetically prepared according to known or customary procedure such as a reaction between an 3-alkyl-3-oxetanemethanol and a methanesulfonyl halide or a halogenation of an 3-alkyl-3-oxetanemethanol, each in the presence of triethylamine and methylene chloride.

In Formula (3), "A" corresponds to "A" in Formula (1) and represents either a linear alkylene group represented by Formula (a1) or a branched-chain alkylene group represented by Formula (a2).

In Formula (a1), n1 denotes an integer of 3 or more. In Formula (a2), $R^3$, $R^4$, $R^7$, and $R^8$ are the same as or different from one another and each represent a hydrogen atom or an alkyl group; $R^5$ and $R^6$ are the same as or different from each other and each represent an alkyl group; and n2 denotes an integer of 0 or more. When n2 is an integer of 2 or more, two or more $R^7$s may be the same as or different from one another, and two or more $R^8$s may be the same as or different from one another. Exemplary alkyl groups as $R^3$, $R^4$, $R^5$, $R^6$, $R^7$, and $R^8$ are as with the alkyl groups as $R^3$, $R^4$, $R^5$, $R^6$, $R^7$, and $R^8$ in the oxetane-ring-containing (meth)acrylic ester compounds represented by Formula (1).

Of compounds represented by Formula (3), compounds in which "A" is a linear alkylene group represented by Formula (a1) are preferably primary alcohols in which n1 is an integer of from 3 to 20, of which primary alcohols in which n1 is an integer of from 3 to 10 are more preferred, because they are easily available.

Of compounds represented by Formula (3), compounds in which "A" is a branched-chain alkylene group represented by Formula (a2) are preferably primary alcohols in which n2 is an integer of from 1 to 20, of which primary alcohols in which n2 is an integer of from 1 to 10 are more preferred, because they provide a high reaction yield in the (meth)acrylation step and are industrially excellent.

Typical examples of compounds represented by Formula (3) in which "A" is a linear alkylene group represented by Formula (a1) include the following compounds:

[Chem. 9]

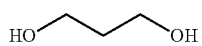

(3-a1-1)

(3-a1-2)

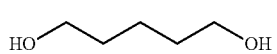

(3-a1-3)

Typical examples of compounds represented by Formula (3) in which "A" is a branched-chain alkylene group represented by Formula (a2) include the following compounds:

[Chem. 10]

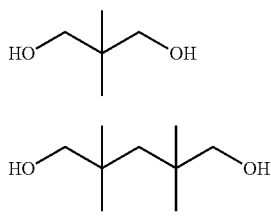

(3-a2-1)

(3-a2-2)

The reaction between the compound represented by Formula (2) and the compound represented by Formula (3) is performed specifically in a single-liquid phase system. As used herein the term "single-liquid phase system" refers to a system including a liquid phase in a number of not two or more but only one, in which the system may also include a solid as long as it includes only one liquid phase. A solvent for use herein may be any one, as long as capable of dissolving both the compound represented by Formula (2) and the compound represented by Formula (3) therein, which is exemplified by aromatic hydrocarbons such as benzene, toluene, xylenes, and ethylbenzene; ethers such as THF (tetrahydrofuran) and IPE (isopropyl ether); sulfur-containing solvents such as DMSO (dimethyl sulfoxide); and nitrogen-containing solvents such as DMF (dimethylformamide).

When a compound represented by Formula (3) in which "A" is a linear alkylene group represented by Formula (a1) is used as the compound represented by Formula (3), the solvent for use herein is preferably any of ethers such as THF (tetrahydrofuran) and IPE (isopropyl ether), of which dehydrated ethers such as dehydrated THF and dehydrated IPE are preferred. This is because such ethers are highly reactive and can be easily extracted into an organic layer.

When a compound represented by Formula (3) in which "A" is a branched-chain alkylene group represented by Formula (a2) is used as the compound represented by Formula (3), the solvent is preferably any of sulfur-containing solvents such as DMSO (dimethyl sulfoxide), and nitrogen-containing solvents such as DMF (dimethylformamide), of which dehydrated DMSO and dehydrated DMF, for example, are more preferred, because the compound is highly soluble in these solvents.

The reaction between the compound represented by Formula (2) and the compound represented by Formula (3) may be carried out typically by adding dropwise a solution of the compound represented by Formula (2) in any of the aforementioned solvents to a solution of the compound represented by Formula (3) in the same solvent.

Examples of the basic substance include hydroxides of alkali metals or alkaline earth metals, such as sodium hydroxide, potassium hydroxide, calcium hydroxide, and magnesium hydroxide; hydrides of alkali metals or alkaline earth metals, such as sodium hydride, magnesium hydride, and calcium hydride; carbonates of alkali metals or alkaline earth metals, such as sodium carbonate and potassium carbonate; hydrogen carbonates of alkali metals or alkaline earth metals, such as sodium hydrogen carbonate and potassium hydrogen carbonate; and organic metallic compounds including organic lithium reagents (e.g., methyllithium, ethyllithium, n-butyllithium, sec-butyllithium, and ter-butyllithium) and organic magnesium reagents (Grignard reagents; e.g., $CH_3MgBr$ and $C_2H_5MgBr$). Each of these may be used alone or in combination. Among them, preferred for use in the present invention are hydrides of alkali metals, such as sodium hydride; and hydroxides of alkali metals, such as sodium hydroxide and potassium hydroxide, because they are satisfactorily soluble in the solvent.

Though varying depending on basic strength, the amount of the basic substance is typically from about 0.5 to about 10.0 times by mole, and preferably from about 0.8 to about 2.0 times by mole, relative to the material compound represented by Formula (2). The basic substance, if used in an amount less than the above range, may cause a larger amount of unreacted material. In contrast, the basic substance, if used in an amount more than the above range, may tend to cause a byproduct compound (diether) to be formed in a higher yield, which byproduct compound corresponds to the target product, except with both the two hydroxyl groups of the compound represented by Formula (3) being etherified.

The amount of the compound represented by Formula (3) may be suitably controlled and is typically from about 1.0 to about 20.0 times by mole, and preferably from about 5.0 to about 20.0 times by mole, relative to the amount of the compound represented by Formula (2).

The reaction temperature may be suitably regulated typically by the rate of dropwise addition of the compound represented by Formula (2) and is typically from about 30° C. to about 150° C., and particularly preferably from about 40° C. to about 120° C. The reaction, if performed at a temperature lower than the range, may often cause larger amounts of unreacted materials. In contrast, the reaction, if performed at a temperature higher than the range, may tend to cause a byproduct compound (diether) to be produced in a higher yield, which byproduct compound corresponds to the target product, except with both the two hydroxyl groups of the compound represented by Formula (3) being etherified.

The reaction between the compound represented by Formula (2) and the compound represented by Formula (3) can synthetically give an oxetane-ring-containing alcohol represented by following Formula (4). The oxetane-ring-containing alcohol is a precursor for an oxetane-ring-containing (meth)acrylic ester compound represented by Formula (1). In Formula (4), $R^1$ corresponds to $R^1$ in Formula (2) and represents a hydrogen atom or an alkyl group; and "A" corresponds to "A" in Formula (3) and represents either a linear alkylene group represented by Formula (a1) or a branched-chain alkylene group represented by Formula (a2).

[Chem. 11]

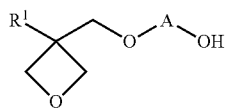

(4)

The present invention, as employing the reaction, can suppress the byproduction of diether in a formation rate of less than 7% (preferably 5% or less, and particularly preferably 1% or less). This allows the selective synthetic preparation of the oxetane-ring-containing alcohol represented by Formula (4) in a high yield of typically 65% or more, preferably 70% or more, and particularly preferably 80% or more.

The oxetane-ring-containing alcohol represented by Formula (4) formed through the reaction may be separated/purified according to a customary separation/purification procedure such as concentration, extraction, crystallization, recrystallization, distillation, or column chromatography, or any combination of them.

Subsequently, the prepared oxetane-ring-containing alcohol represented by Formula (4) is (meth)acrylated and thereby yields an oxetane-ring-containing (meth)acrylic ester compound represented by Formula (1) according to the present invention. The (meth)acrylation may be performed, for example, by allowing (meth)acrylic acid or a derivative thereof to react with the alcohol. The oxetane-ring-containing (meth)acrylic ester compound represented by Formula (1) may be produced in a yield of typically 65% or more, and preferably 70% or more.

Examples of the (meth)acrylic acid derivative include derivatives capable of reacting with an alcohol to give a corresponding ester, which are typified by corresponding acyl halides such as acyl chloride; acid anhydrides; and esters (e.g., alkyl esters and alkenyl esters), such as methyl ester, ethyl ester, vinyl ester, and 2-propenyl ester.

(Meth)acrylic acid or a derivative thereof may be used in an amount of typically from about 1.0 to about 10.0 times by mole, and preferably from about 1.0 to about 3.0 times by mole, relative to the amount of the oxetane-ring-containing alcohol represented by Formula (4).

The reaction of (meth)acrylation is generally performed in a solvent inert to the reaction. Examples of the solvent include halogenated hydrocarbons such as methylene chloride, chloroform, 1,2-dichloroethane, chlorobenzene, trifluoromethylbenzene, and carbon tetrachloride; aromatic hydrocarbons such as benzene, toluene, xylenes, and ethylbenzene; and ethers such as THF (tetrahydrofuran) and IPE (isopropyl ether).

The (meth)acrylation is preferably performed in the presence of a basic substance. Exemplary basic substances include tertiary amine compounds such as trimethylamine, triethylamine, trimethanolamine, and triethanolamine; nitrogen-containing aromatic heterocyclic compounds such as pyridine; and organic metallic compounds including organic lithium reagents (e.g., methyllithium, ethyllithium, n-butyllithium, sec-butyllithium, and ter-butyllithium) and organic magnesium reagents (Grignard reagents; e.g., $CH_3MgBr$ and $C_2H_5MgBr$).

The (meth)acrylation reaction may be performed under normal atmospheric pressure, under a pressure (under a load), or under reduced pressure at a reaction temperature of typically from about −40° C. to about 150° C., and preferably from about −10° C. to about 30° C. For suppressing a polymerization reaction, the reaction system may further include a polymerization inhibitor or polymerization retarder, such as hydroquinone, methoxyphenol, or an oxygen-containing gas.

The oxetane-ring-containing (meth)acrylic ester compound represented by Formula (1) and formed by the reaction may be separated/purified according to a customary separation/purification procedure such as concentration, extraction, crystallization, recrystallization, distillation, or column chromatography, or any combination of them.

EXAMPLES

The present invention will be illustrated in further detail with reference to several working examples below. It should be noted, however, that these examples are never construed to limit the scope of the present invention.

Example 1

Synthesis of 3-ethyl-3-(4-acryloyloxybutyloxymethyl)oxetane

In a nitrogen atmosphere, 3-ethyl-3-oxetanemethanol (100 g), methylene chloride (1000 g), and triethylamine (113 g) were placed in a four-necked flask, followed by stirring at room temperature (25° C.). To this, was added dropwise methanesulfonyl chloride (108 g) over one hour. After dropwise addition, the mixture was subjected to a reaction at room temperature (25° C.) for one hour. The resulting reaction mixture was combined with 400 g of ion-exchanged water, separated into two liquid layers, from which the methylene chloride layer was recovered, concentrated, elded 3-ethyl-3-methanesulfonyloxymethyloxetane (170 g, in a yield of 99%).

In a nitrogen atmosphere, 55% sodium hydride (7.4 g) and dehydrated THF (120 g) were placed in a four-necked flask, followed by stirring at room temperature (25° C.). To this, was added dropwise a solution of 1,4-butanediol (83.5 g) in dehydrated THF (91 g) over 20 minutes. After checking that heat generation and gassing ceased, the reaction mixture was raised in temperature to 60° C., followed by stirring for one hour. Thereafter a solution of the above-prepared 3-ethyl-3-methanesulfonyloxymethyloxetane (30 g) in dehydrated THF (212 g) was added dropwise over 45 minutes, and after dropwise addition, the mixture was allowed to react for further 12 hours. The liquid layer was not separated but remained uniform during the reaction.

The reaction mixture was then cooled, combined with ion-exchanged water (150 g), and separated into two liquid layers, from which the THF layer was recovered. The THF layer was concentrated. The concentrate was purified through silica gel column chromatography and thereby yielded 3-ethyl-3-(4-hydroxybutyloxymethyl)oxetane (32.1 g, in a yield of 81%).

In a nitrogen atmosphere, the above-prepared 3-ethyl-3-(4-hydroxybutyloxymethyl)oxetane (30.0 g), methylene chloride (300 g), and triethylamine (24.8 g) were placed in a four-necked flask, stirred, and cooled to 2° C. Thereafter acryloyl chloride (18.7 g) was added dropwise over one hour, followed by a reaction for further one hour.

The reaction mixture was combined with ion-exchanged water (300 g) and separated into two liquid layers, from which the methylene chloride layer was recovered. The residual aqueous layer was re-extracted with methylene chloride (150 g), and the methylene chloride layers were collected, combined, and concentrated. The concentrate was purified through silica gel column chromatography and thereby yielded 3-ethyl-3-(4-acryloyloxybutyloxymethyl)oxetane (28.7 g, in a yield of 74%) represented by the following formula.

$^1$H-NMR (500 MHz, $CDCl_3$) δ 6.40 (1H, dd), 6.12 (1H, q), 5.82 (1H, dd), 4.45 (2H, d), 4.38 (2H, d), 4.18 (2H, t), 3.53 (2H, s), 3.49 (2H, t), 1.76 (4H, m), 1.67 (2H, m), 0.88 (3H, t)

[Chem. 13]

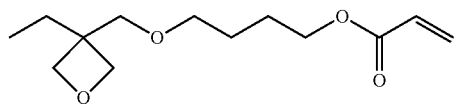

Example 2

Example 2

A mixture of 2-(1-methoxy)propyl acetate (PGMEA) (11.63 g), 3-ethyl-3-(4-acryloyloxybutyloxymethyl)oxetane prepared in Example 1 (2.26 g: 8.25 mmol), and 2,2'-azobisisobutyronitrile (AIBN) (0.14 g) was placed in a Schlenk tube, uniformized by stirring, and heated with stirring at 75±1° C. for 5 hours. This was cooled, purified through reprecipitation from a five-fold amount of heptane, held in a vacuum dryer (40° C., full vacuum) for 15 hours, and thereby yielded a liquid resin (1) which is colorless and transparent at room temperature (25° C.). The liquid resin (1) has a weight-average molecular weight of 21500 and a number-average molecular weight of 8300 each determined in terms of polystyrene standard through gel permeation chromatography (GPC).

Next, a mixed solution (1) was prepared by mixing 100 parts by weight of the above-prepared liquid resin (1) with 3 parts by weight of a photo-induced cationic polymerization initiator (trade name "CPI-100P", supplied by SAN-APRO LIMITED).

Example 3

Synthesis of 3-ethyl-3-(3-acryloyloxy-2,2-dimethyl-propyloxymethyl)oxetane

In a nitrogen atmosphere, 3-ethyl-3-oxetanemethanol (100 g), methylene chloride (1000 g), and triethylamine (113 g) were placed in a four-necked flask, followed by stirring at room temperature (25° C.). Next, methanesulfonyl chloride (108 g) was added dropwise over one hour. After dropwise addition, the mixture was subjected to a reaction at room temperature (25° C.) for one hour. After the reaction, the reaction mixture was combined with ion-exchanged water (400 g), separated into two liquid layers, from which the methylene chloride layer was recovered, concentrated, and thereby yielded 3-ethyl-3-methanesulfonyloxymethyloxetane (170 g).

In a nitrogen atmosphere, 55% sodium hydride (11.3 g) and dehydrated DMSO (150 g) were placed in a four-necked flask, followed by stirring at room temperature (25° C.). This solution was combined with a solution of neopentyl glycol (160 g) in dehydrated DMSO (250 g) added dropwise over 30 minutes. After checking that heat generation and gassing ceased, the reaction mixture was raised in temperature to 60° C., followed by stirring for one hour. A solution of the above-prepared 3-ethyl-3-methanesulfonyloxymethyloxetane (50 g) in dehydrated DMSO (100 g) was then added dropwise over 60 minutes, and after dropwise addition, the mixture was allowed to react for further one hour. The liquid layer during the reaction was not separated but remained uniform.

Next, after being cooled, the reaction mixture was combined with ion-exchanged water (200 g) and IPE (200 g), from which the IPE layer was recovered. In addition, the aqueous layer was extracted with IPE four times, and the IPE layers were collected, combined, and concentrated. The concentrate was purified through silica gel column chromatography and thereby yielded 3-ethyl-3-(3-hydroxy-2,2-dimethylpropyloxymethyl)oxetane (42.7 g, in a yield of 81%).

In a nitrogen atmosphere, the above-prepared 3-ethyl-3-(3-hydroxy-2,2-dimethylpropyloxymethyl)oxetane (40 g), methylene chloride (400 g), and triethylamine (31 g) were placed in a four-necked flask, stirred, and cooled to 2° C. Acryloyl chloride (23.3 g) was then added dropwise over one hour, followed by a reaction for further one hour.

The reaction mixture was combined with ion-exchanged water (400 g) and separated into two liquid layers, from which the methylene chloride layer was recovered. The residual aqueous layer was further re-extracted with methylene chloride (200 g), the methylene chloride layers were collected, combined, and concentrated. The concentrate was purified through silica gel column chromatography and thereby yielded 3-ethyl-3-(3-acryloyloxy-2,2-dimethylpropyloxymethyl)oxetane (42.6 g, in a yield of 88%) represented by the following formula.

$^1$H-NMR (500 MHz, CDCl$_3$) δ 6.39 (1H, d), 6.13 (1H, q), 5.83 (1H, dd), 4.44 (2H, d), 4.36 (2H, d), 3.98 (2H, s), 3.52 (2H, s), 3.23 (2H, s), 1.73 (2H, q), 0.96 (6H, t), 0.86 (3H, t)

[Chem. 14]

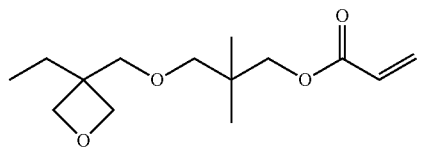

Example 4

A mixture of 2-(1-methoxy)propyl acetate (PGMEA) (4.80 g), 3-ethyl-3-(3-acryloyloxy-2,2-dimethylpropyloxymethyl)oxetane (2.07 g: 7.80 mmol) prepared in Example 3, and AIBN (0.0605 g) was placed in a Schlenk tube, uniformized by stirring, and heated with stirring at 75±1° C. for 5 hours. After being cooled, this was purified through reprecipitation from a five-fold amount of heptane, held in a vacuum dryer (40° C., full vacuum) for 15 hours, and thereby yielded a liquid resin (2) which is colorless and transparent at room temperature (25° C.). The liquid resin (2) has a weight-average molecular weight of 37600 and a number-average molecular weight of 14200, each determined in terms of polystyrene standard through gel permeation chromatography (GPC).

Next, a mixed solution (2) was prepared by mixing 100 parts by weight of the above-prepared liquid resin (2) with 3 parts by weight of a photo-induced cationic polymerization initiator (trade name "CPI-100P", supplied by SAN-APRO LIMITED).

Comparative Example 1

A mixture of 2-(1-methoxy)propyl acetate (PGMEA) (12.05 g), 3-ethyl-3-(2-acryloyloxyethyloxymethyl)oxetane (2.24 g: 9.25 mmol), and AIBN (0.14 g) was placed in a Schlenk tube, uniformized by stirring, and heated with stirring at 75±1° C. for 5 hours. After being cooled, this was purified through reprecipitation from a five-fold amount of heptane, held in a vacuum dryer (40° C., full vacuum) for 15 hours, and thereby yielded a liquid resin (3) which is colorless and transparent at room temperature (25° C.). The liquid resin (3) has a weight-average molecular weight of 18000 and a number-average molecular weight of 6000, each determined in terms of polystyrene standard through gel permeation chromatography (GPC).

Next, a mixed solution (3) was prepared by mixing 100 parts by weight of the above-prepared liquid resin (3) with 3 parts by weight of a photo-induced cationic polymerization initiator (trade name "CPI-100P", supplied by SAN-APRO LIMITED).

Evaluations

The mixed solutions (1), (2), and (3) prepared in Examples 2 and 4 and Comparative Example 1 were polymerized according to a method mentioned below to give cured articles, and the cured articles were examined on flexibility and thermal stability according to methods mentioned below.

[Formation of Cured Articles]

The mixed solutions (1), (2), and (3) prepared in Examples 2 and 4 and Comparative Example 1 were each applied to a thickness of about 100 μm to a fluorine-coated PET (poly(ethylene terephthalate)) base film using an applicator, irradiated with an ultraviolet ray using a belt-conveyer type ultraviolet irradiator (UVC-02516S1AA02, supplied by Ushio Inc.), heated at 100° C. in the atmosphere for one hour, and thereby yielded cured articles (1), (2), and (3), respectively. The irradiation was performed at an irradiation energy of about 2 J (wavelength: 320 to 390 nm).

[Evaluation of Flexibility]

The cured articles (1) and (3) prepared according to the above method were each placed around a rod 1 mm in radius under conditions of a temperature of 20° C. and relative humidity of 50%, whether the samples showed cracks (cracking) or not was visually observed, and the flexibility (bendability) of the samples was evaluated according to the following criteria.

Criteria:
No cracking is observed: Good
Cracking is observed: Inferior

[Measurement of Modulus of Elasticity]

The cured articles (1) and (3) prepared according to the above method were each examined on dynamic viscoelasticity at 20° C. using a viscoelastometer (rheometer) (trade name "RSA III", supplied by Rheometric Scientific F. E. Ltd. (now TA Instruments)) and the modulus of elasticity was evaluated according to the following criteria:

Criteria:
Modulus of elasticity (GPa) is 1.0 or less: Good
Modulus of elasticity (GPa) is more than 1.0: Inferior The results are collectively shown in Table 1 below.

TABLE 1

| | | Example 1 | Comparative Example 1 |
|---|---|---|---|
| Mixed solution | Liquid resin (1) | 100 | — |
| | Liquid resin (3) | — | 100 |
| | Photo-induced cationic polymerization initiator | 3 | 3 |
| Evaluations | Flexibility | Good | Inferior |
| | Modulus of elasticity | Good | Inferior |

Table 1 demonstrates that the cured article obtained from the oxetane-ring-containing (meth)acrylic ester compound according to the present application, represented by Formula (1) in which "A" is a linear alkylene group represented by Formula (a1) having three or more carbon atoms, has more satisfactory flexibility than that of the cured article obtained from the oxetane-ring-containing (meth)acrylic ester compound having a structure including an oxetane ring and a (meth)acryloyl group bonded to each other through the medium of an alkylene group having two or less carbon atoms.

[Evaluation of Thermal Stability]

The cured articles (2) and (3) were subjected to thermogravimetry with a thermal analyzer (trade name "TG-DTA 6300", supplied by Seiko Electronic Industry Co., Ltd. (now Seiko Instruments Inc.)). With reference to FIG. 1, a pyrolysis temperature T (° C.) was defined as a temperature at the point where the tangent line of a region with no weight loss or gradual weight loss in early stages of temperature rise intersects with the tangent line of the inflection point of a region with abrupt weight loss. Based on this, the thermal stability of the samples was evaluated according to the following criteria.

Criteria:
Pyrolysis temperature T (° C.) is 365° C. or higher: Good
Pyrolysis temperature T (° C.) is lower than 365° C.: Inferior The results are collectively shown in Table 2 below.

TABLE 2

| | | Example 4 | Comparative Example 1 |
|---|---|---|---|
| Mixed solution | Liquid resin (2) | 100 | — |
| | Liquid resin (3) | — | 100 |
| | Photo-induced cationic polymerization initiator | 3 | 3 |
| | Pyrolysis temperature | Good | Inferior |

Table 2 demonstrates that the cured article obtained from the oxetane-ring-containing (meth)acrylic ester compound according to the present application represented by Formula (1), in which "A" is a branched-chain alkylene group represented by Formula (a2) and having a tetrasubstituted carbon at the 6-position from the carbon of (meth)acrylic terminus, has more satisfactory thermal stability than that of the cured article obtained from the oxetane-ring-containing (meth) acrylic ester compound having a disubstituted carbon at the 6-position from the carbon of (meth)acrylic terminus.

Industrial Applicability

Oxetane-ring-containing (meth)acrylic ester compounds represented by Formula (1) according to the present invention can give, through polymerization, cured articles having furthermore satisfactory flexibility or thermal stability. The compounds are therefore advantageously usable typically in the fields of waveguides, optical fibers, base films and protective films for solar cells, base films and protective films for flexible displays, base films and protective films for organic electroluminescent devices, transparent sealants, adhesives, ink-jet inks, color filters, nanoprinting (materials), and flexible wiring boards.

The invention claimed is:

1. An oxetane-ring-containing (meth)acrylic ester compound represented by Formula (1):

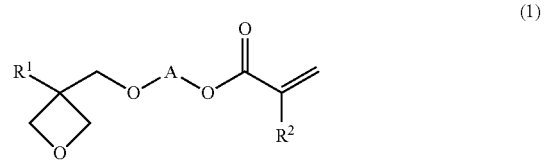

(1)

wherein $R^1$ represents a hydrogen atom or an alkyl group; $R^2$ represents a hydrogen atom or a methyl group; "A" represents either a linear alkylene group represented by Formula (a1) or a branched-chain alkylene group represented by Formula (a2):

(a1)

(a2)

wherein, in Formula (a1), n1 denotes an integer of 4 to 20, and in Formula (a2), $R^3$, $R^4$, $R^7$, and $R^8$ are the same as or different from one another and each represent a hydrogen atom or an alkyl group; $R^5$ and $R^6$ are the same as or different from each other and each represent an alkyl group; and n2 denotes an integer of 1 to 20, wherein, when n2 is an integer of 2 or more, two or more $R^7$s may be the same as or different from one another, and two or more $R^8$s may be the same as or different from one another, and wherein the terminal carbon closest to $R^4$ of Formula (a2) is bonded to oxygen atom constituting ester bond.

2. A process for producing an oxetane-ring-containing (meth)acrylic ester compound, the process comprising the steps of: allowing two compounds to react with each other in the presence of a basic substance in a single-liquid phase system to give a reaction product; and (meth)acrylating the reaction product to synthetically prepare the oxetane-ring-containing (meth)acrylic ester compound, wherein
one of the two compounds being represented by Formula (2):

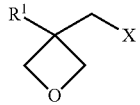

(2)

wherein $R^1$ represents a hydrogen atom or an alkyl group; and X represents a leaving group,
the other compound being represented by Formula (3):

HO-A-OH    (3)

wherein "A" represents either a linear alkylene group represented Formula (a1) or a branched-chain alkylene group represented by following Formula (a2):

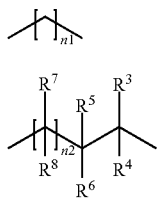

(a1)

(a2)

wherein, in Formula (a1), n1 denotes an integer of 3 or more, and in Formula (a2), $R^3$, $R^4$, $R^7$; and $R^8$ are the same as or different from one another and each represent a hydrogen atom or an alkyl group; $R^5$ and $R^6$ are the same as or different from each other and each represent an alkyl group; and n2 denotes an integer of 0 or more, wherein, when n2 is an integer of 2 or more, two or more $R^7$s may be the same as or different from one another, and two or more $R^8$s may be the same as or different from one another, and
the oxetane-ring-containing (meth)acrylic ester compound being represented by Formula (1):

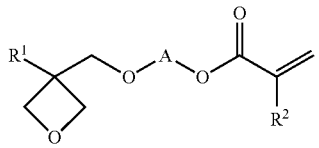

(1)

wherein $R^2$ represents a hydrogen atom or a methyl group; and $R^1$ and A are as defined above.

3. An oxetane-ring-containing alcohol which is represented by Formula (4):

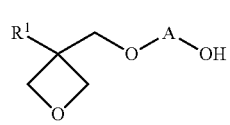

(4)

wherein $R^1$ represents a hydrogen atom; "A" represents either a linear alkylene group represented by Formula (a1) or a branched-chain alkylene group represented by Formula (a2):

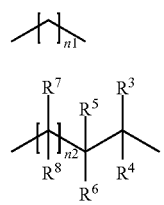

(a1)

(a2)

wherein, in Formula (a1), n1 denotes an integer of 3 or more, and, in Formula (a2), $R^3$, $R^4$, $R^7$, and $R^8$ are the same as or different from one another and each represent a hydrogen atom or an alkyl group; $R^5$ and $R^6$ are the same as or different from each other and each represent an alkyl group; and n2 denotes an integer of 0 or more, wherein, when n2 is an integer of 2 or more, two or more $R^7$s may be the same as or different from one another, and two or more $R^8$s may be the same as or different from one another or which is 3-ethyl-3-(3-hydroxy-2,2-dimethylpropyloxymethyl)oxetane.

4. A process for producing an oxetane-ring-containing alcohol, the process comprising the step of allowing two compounds to react with each other in the presence of a basic substance in a single-liquid phase system to give the oxetane-ring-containing alcohol,
one of the two compounds being represented by Formula (2):

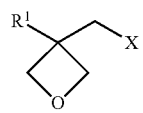

(2)

wherein $R^1$ represents a hydrogen atom; and X represents a leaving group,
the other compound being represented by Formula (3):

HO-A-OH (3)

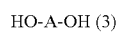

wherein "A" represents either a linear alkylene group represented by Formula (a1) or a branched-chain alkylene group represented by Formula (a2):

(a1)

-continued

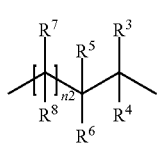
(a2)

wherein, in Formula (a1), n1 denotes an integer of 3 or more, and, in Formula (a2), $R^3$, $R^4$, $R^7$, and $R^8$ are the same as or different from one another and each represent a hydrogen atom or an alkyl group; $R^5$ and $R^6$ are the same as or different from each other and each represent an alkyl group; and n2 denotes an integer of 0 or more, wherein, when n2 is an integer of 2 or more, two or more $R^7$s may be the same as or different from one another, and two or more $R^8$s may be the same as or different from one another, and the oxetane-ring-containing alcohol being represented by Formula (4):

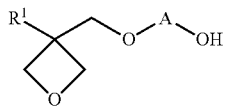
(4)

wherein $R^1$ and A are as defined above or being 3-ethyl-3-(3-hydroxy-2,2-dimethylpropyloxymethyl)oxetane.

* * * * *